United States Patent
Zhu et al.

[11] Patent Number: 6,102,921
[45] Date of Patent: Aug. 15, 2000

[54] NERVE ANASTOMOSIS SLING AND METHOD

[75] Inventors: Yong Hua Zhu; Wolff M. Kirsch, both of Albuquerque; Robert B. Cushman, Cedar Crest, all of N. Mex.

[73] Assignee: University of New Mexico, Albuquerque, N. Mex.

[21] Appl. No.: 07/631,954

[22] Filed: Dec. 21, 1990

[51] Int. Cl.$^7$ .................................................. A61B 17/08
[52] U.S. Cl. ........................................................ 606/152
[58] Field of Search ........................... 606/139–144, 606/152–155

[56] References Cited

U.S. PATENT DOCUMENTS

| | | |
|---|---|---|
| 4,534,349 | 8/1985 | Barrows . |
| 4,586,504 | 5/1986 | de Medinaceli . |
| 4,669,474 | 6/1987 | Barrows . |
| 4,870,966 | 10/1989 | Dellon et al. . |
| 4,877,029 | 10/1989 | Valentini et al. . |
| 4,883,618 | 11/1989 | Barrows . |
| 4,920,962 | 5/1990 | Proulx . |

*Primary Examiner*—Michael Buiz
*Assistant Examiner*—Mark Leonardo

[57] ABSTRACT

A medical anastomosis sling for use in the repair or regeneration of nerves. Nerve ends are placed in a breathable semiporous membrane having sets of elongate and wide tabs which are secured and sealed around the ends via circumferential fasteners and surgical clips for securing and sealing the sling in position without the necessity of suturing the device for optimal anastomosis.

10 Claims, 2 Drawing Sheets

NERVE ANASTOMOSIS SLING AND METHOD

BACKGROUND OF THE INVENTION

This invention relates to medical devices useful for the anastomosis of injured or lacerated nerves, and to a method for rejoining the ends or stumps of lacerated or severed nerves, such as peripheral nerves.

The repair of lacerated or severed peripheral nerves, using sutures or tubes, is a common surgical procedure. The use of these procedures has enhanced the surgeon's ability to replant amputated body parts, to achieve composite tissue transfer, and to graft nerves. The current procedures usually involve penetration of the nerve with needle or suture. Such penetration results in the formation of scar tissue which significantly inhibits anastomosis of the nerve ends preventing nerve regeneration or reconnection.

Tubes, which are commonly used to reconnect nerve ends, are not adjustable in diameter and are almost impossible to select for perfect fit over a nerve. If the tube is too small, the nerve is traumatized and swells. If the tube is too large, there is bad anastomosis. It is impossible to provide a spectrum of tubes which afford a perfect fit and optimal anastomosis.

One sutureless nerve repair device and method involves use of a rough surfaced two piece tube. This device and method is discussed in U.S. Pat. Nos. 4,534,349, 4,669,474, and 4,883,618. These devices are body absorbable, and tubular in structure. They operate on a friction type fit and do not provide the spectrum of sizes require for proper fit and optimal anastomosis.

Further, U.S. Pat. No. 4,586,504 discloses a method and device whereby a flexible, inelastic sheet is used as a basis for suturing nerve ends together with guidelines to instruct surgeons precisely how much tissue must be trimmed from the stumps of severed nerves. This device requires suturing of the nerve ends and enhances unwanted scar tissue formation.

U.S. Pat. No. 4,870,966 discloses a bioabsorbable tube for repair of nerve defects or gaps. This device also has the differences of tube size and fit.

The prior art falls well short of the novel sling device and method for regenerating nerve ends embodied by the present invention.

The present state of the art falls well short of the necessity to provide an adjustable, breathable, semipermeable, porous sutureless sling for the optimal anastomosis of peripheral nerves or the like.

SUMMARY OF THE INVENTION

It is an object of the present invention to provide a unique breathable semipermeable porous sling, which provides an optimum environment for nerve regrowth and/or regeneration across nerve gaps without the use of sutures or needles, thereby overcoming the problem of scar tissue promotion which interferes with nerve regeneration.

It is an object of the present invention to provide a unique breathable semipermeable porous sling, which can be adjusted to fit securely over nerves of almost any diameter in a totally non-penetrating fashion.

A further object of the present invention is to provide a unique breathable semipermeable porous sling, which allows diffusion of metabolites in and out of the nerve without having scar tissue constrict or compromise the nerve nutritionally.

A further object of the present invention is to provide a unique breathable semipermeable porous sling which can be impregnated with specific growth factors such as nerve growth factor. The use of nerve growth factor promotes the regrowth of nerve fibers and facilitates healing in systems that have been difficult to treat.

A further object of the present invention is to provide a process whereby nerve ends or stumps are regenerated or reconnected in an enhanced sutureless environment.

The present invention provides a unique sling device for the anastomosis or repair of peripheral nerves. The breathable semipermeable porous membrane structure is constructed with unique elongate and wide tabs which are secured by circumferential fasteners and surgical mini or micro clips to form an enhanced secure environment. The sling allows metabolites to pass in and out of the nerves facilitating growth without scar tissue constriction which normally is present and acts to comprise anastomosis.

Further, the sling can be impregnated with nerve growth factor to promote regrowth and regeneration of the nerve. Circumferential fasteners and micro or mini surgical clips are utilized to secure and seal the sling and can be constructed of any suitable material.

The unique adjustable configuration of the sling allows it to be used for nerves of all thicknesses, shapes and sizes. The unique combination of the circumferential fasteners, which enables the device to be adjusted and secured, and micro or mini surgical clips, which act to seal thle device without suture, provide a perfect environment for anastomosis to occur.

The sling's flexibility allows the device to pass over joints or areas where bending of the regenerating nerve will occur, without traumatizing the site to be treated.

The sling is utilized to optimally allow for the anastomosis of nerves whereby the nerve stumps or ends are layed directly onto the body of the breathable porous sling. The body of the sling is then wrapped around the nerve stumps mating the sets of tabs which are present along the sling body. Circumferential fasteners are placed over the two end sets of elongate tabs and tightened until no slack is left between the mated tabs and the body of the sling. The two sets of elongate tabs are trimmed and sealed securely by surgical mini or micro clips. Simultaneously, the wide central tabs are interlocked and sealed by a plurality of mini or micro clips, as needed.

If desired, the sling can be preimpregnated with nerve growth factor to simulate reconnection or regeneration of the nerve ends.

DETAILED DESCRIPTION OF THE PREFERRED EMBODIMENTS

Figure 1:
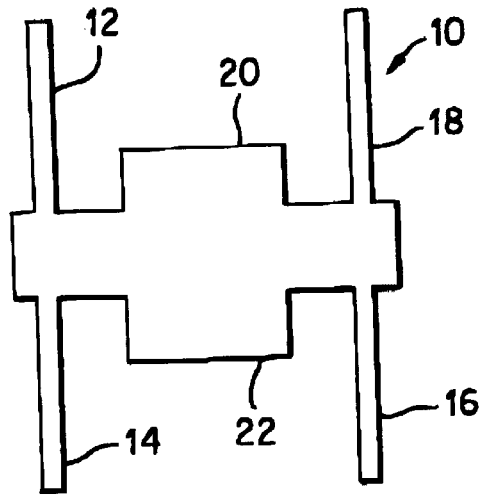
FIG. 1 is a view of the nerve anastomosis sling embodying the present invention.

FIG. 1 illustrates the nerve anastomosis sling 10 embodying the present invention. The sling 10 is composed of a breathable porous membrane material and has two sets of elongate tabs (12, 14) and (16, 18) located at a point near the two ends of the sling and a central wide set of tabs (20, 22) located between said first and second set of tabs.

Figure 2:
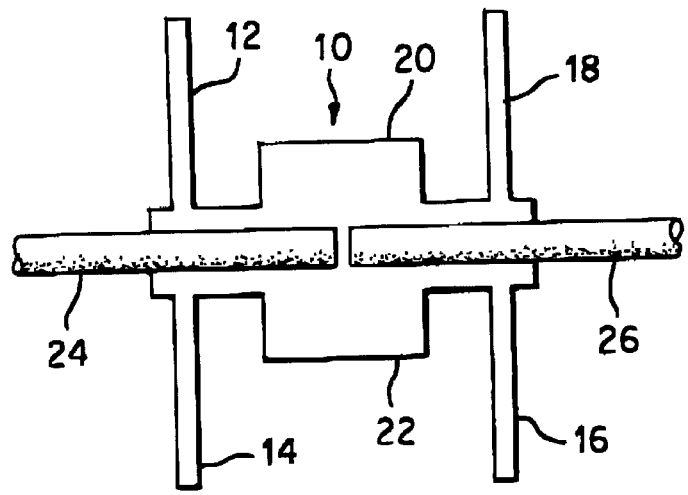
FIG. 2 is a view of the nerve anastomosis sling aligned beneath two nerve ends to be reconnected.

FIG. 2 illustrates the placement of two nerve ends (24, 26) which are seated onto the body of the nerve anastomosis sling 10 for treatment.

Figure 3:
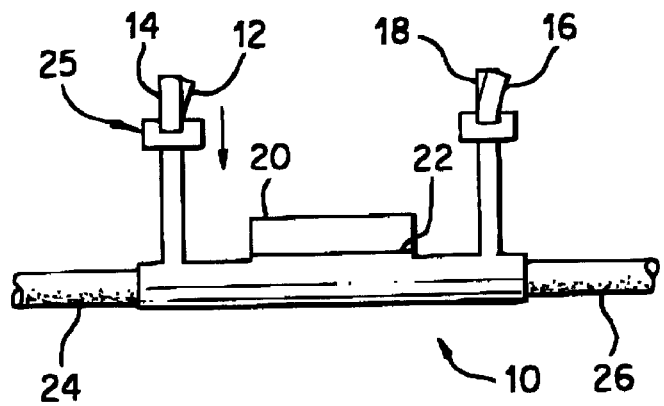
FIG. 3 depicts the nerve anastomosis sling wrapped around two nerve ends with fasteners being positioned into place for securing the sling.

Further, FIG. 3 illustrates the sling 10 enclosing the nerve ends 24 and 26 whereby the tabs 12 and 14, 16 and 18, and 20 and 22 are mated, or interlocked, as illustrated. The mated sets of tabs 12 and 14, and 16 and 18 are secured by placement of circumferential fasteners 24 and 26 thereon, respectively.

Figure 4:
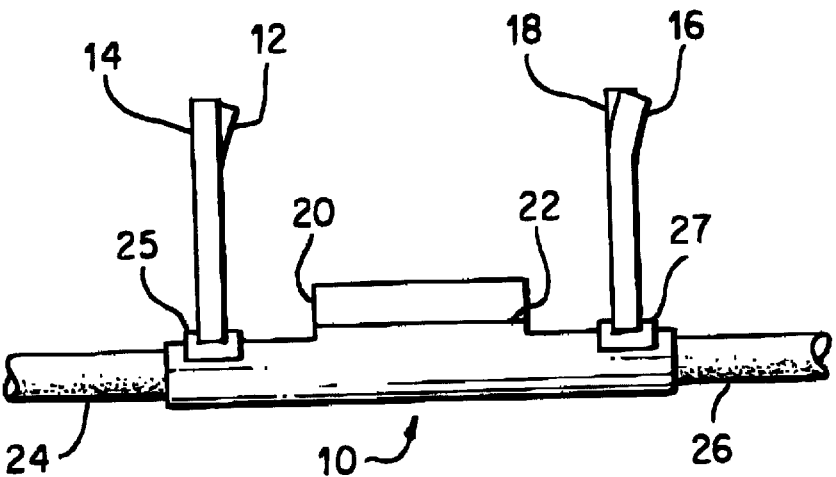
FIG. 4 depicts the nerve anastomosis sling wrapped around two nerve ends with fasteners in place for securing the sling.

FIG. 4 is an illustration of circumferential fasteners 25 and 27, positioned in place for securing tabs 12 and 14, and 16 and 18 in a secure engagement.

Figure 5:
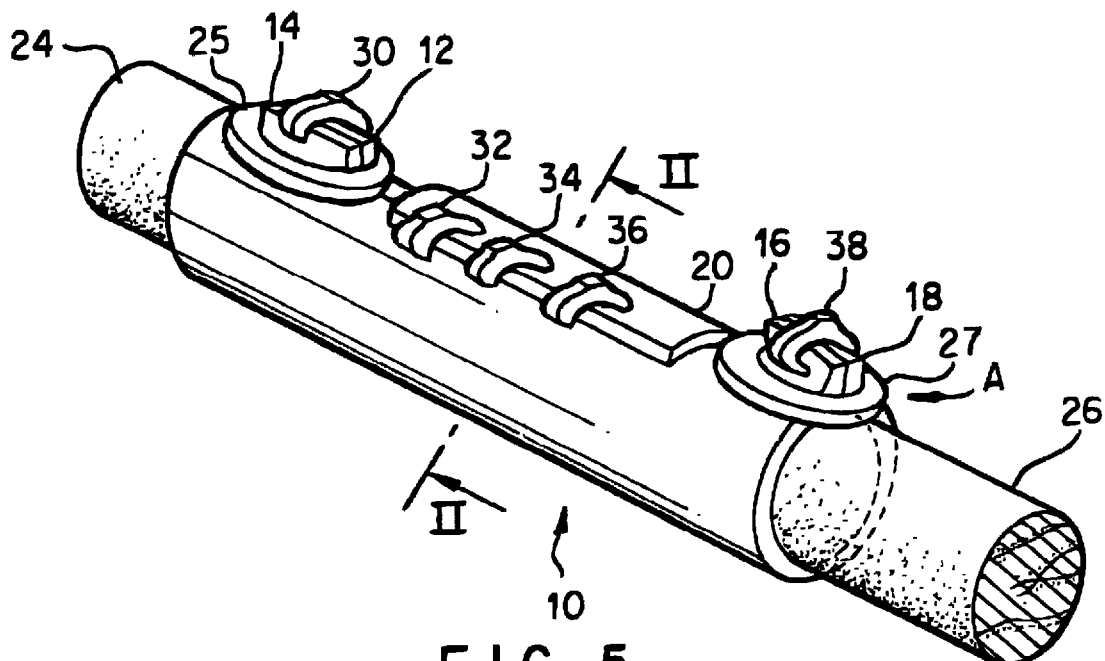
FIG. 5 is a perspective view of the sling embodying the invention wrapped around two nerve ends with clips and fasteners in place.

Finally, FIG. 5 is a perspective view of the sling 10 positioned in place enclosing two nerve ends 24 and 26. Tabs 12 and 14 are securely held together by circumferential fastener 25 and sealed by surgical clip 30. Tabs 16 and 18 are securely held together by circumferential fastener 27 and sealed by surgical clip 38. The elongate tabs 12, 14, 16 and 18 have been manicured to facilitate sealing with surgical clips 30 and 38.

Figure 6:
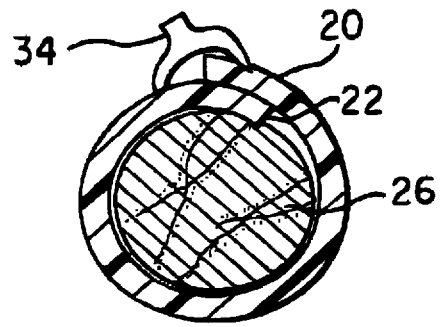
FIG. 6 is a cross sectional view taken along line II—II in FIG. 5.

Further, the wide central tabs 20 and 22 are interlocked, as can be seen by the cutaway in FIG. 6 and are sealed together by surgical clips 32, 34 and 36.

The sling device is preferably produced from a breathable porous semipermeable membrane material such as a fluorocarbon polymer like Teflon or a combination of this material and Gore-Tex. The membrane material being preferably four hundred microns thick and having pores sized around 30 microns. These thicknesses and pore sizes can be adjusted to suit the particular environment.

The use of this novel breathable porous semipermeable material has several advantages. It can be impregnated with specific growth factors, such as nerve growth factor (NGF). NGF promotes the regrowth of nerve fibers and facilitates healing in systems that are considered very difficult. Further, the materials allow metabolites to pass therethrough thereby providing needed nutrition to the site, while keeping scar tissue away.

Further, the sling preferably contains three sets of tabs, two sets elongate in nature and one central wide set located therebetween. The elongate tabs are used to facilitate circumferential fasteners which assists in securing the tabs together. Alternatively, the sling can contain as little as one set of tabs elongate or wide in nature. The location of the tabs can be selected based on the gap and thickness of the site and nerve ends, respectively.

The elongate tabs and/or central wide tabs are secured by micro or mini surgical clips. The combination of micro or mini surgical clips and circumferential fasteners obviate the need for sutures and provide a snug fit. The sling is non-penetrating in nature and can be aligned with nerve ends without penetration of the nerve with needle or syringe.

Furthermore, the sling material enables the anastomosis of nerves that are literally waving in the breeze.

The novel sling 10 is positioned in such a fashion whereby two nerve ends or stumps (24 and 26) are aligned and placed on its body (see FIG. 2). The sling 10 is then wrapped around the nerve ends or stumps (24 and 26) and aligned with tabs [(12, 14) and (16, 18)] in face-to-face engagement. Circumferential fasteners (25 and 27) are then placed over the aligned tabs (12, 14) and (16, 18), respectively to secure the sling 10. The elongate aligned tabs (12, 14) and (16, 18) are then trimmed and the wide central tabs (20, 22) are simultaneously mated for the final sealing process (see FIG. 6). As depicted in FIG. 5, the sling 10 is sealed by surgical clips (30, 32, 34, 36 and 38) to facilitate nerve anastomosis. If desired, the sling 10 can be preimpregnated with nerve growth stimuli such as nerve growth factor prior to the procedure.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A medical anastomosis sling for use in the repair or regeneration of nerves comprising a sling formed of breathable flexible porous semipermeable membrane material having a plurality of tabs spaced thereon for sutureless fastening whereby said sling being capable of enclosing, holding in approximation, and protecting the ends of a lacerated or severed nerve, said medical anastomosis sling having surgical circumferential fasteners and clips for sutureless securing and sealing of said tabs.

2. A medical anastomosis sling as claimed in claim 1 wherein said breathable porous semipermeable membrane material is 400 microns in thickness.

3. A medical anastomosis sling as claimed in claim 1 wherein said breathable porous semipermeable membrane material has pores 30 microns in size.

4. A medical anastomosis sling as claimed in claim 1 wherein said sling having a first and second end has three sets of tabs, one set of tabs located near the first end of said sling and a second set of tabs located near the second end of said sling and a central set of wide tabs located between said first and second sets of tabs.

5. A medical anastomosis sling as claimed in claim 4 wherein said first and second set of tabs is secured by a plurality of circumferential fasteners.

6. A medical anastomosis sling as claimed in claim 5 wherein said first, second, and central set of tabs is further sealed by a plurality of surgical clips.

7. A medical anastomosis sling as claimed in claim 5 further comprising a nerve growth factor incorporated into said breathable semipermeable membrane material to promote the regrowth of nerve fibers and facilitate healing of the nerve ends contained therein.

8. A medical anastomosis sling for use in the repair or regeneration of nerves comprising a sling formed of breathable flexible porous semipermeable membrane material having a plurality of tabs spaced thereon for sutureless fastening whereby said sling being capable of enclosing, holding in approximation, and protecting the ends of a lacerated or severed nerve, said anastomosis sling having a nerve growth factor incorporated into said breathable semipermeable membrane material to promote the regrowth of nerve fibers and facilitate healing of the nerve ends contained therein.

9. A medical anastomosis sling for use in the repair or regeneration of nerves comprising a sling formed of breathable flexible porous semipermeable membrane material having a plurality of tabs spaced thereon for sutureless fastening whereby said sling being capable of enclosing, holding in approximation, and protecting the ends of a lacerated or severed nerve, wherein said breathable porous membrane material is a fluorocarbon polymer.

10. A medical anastomosis sling for use in the repair or regeneration of nerves comprising a sling, formed of breathable porous semipermeable material, having a first and a second end;

two sets of elongate tabs located on said semipermeable material near said first and second ends, respectively.

a central wide set of tabs located on said semipermeable material between said first and second sets of elongate tabs; circumferential fasteners for securing said two sets of elongate tabs located at said first and second ends; and surgical clips for sealing said first, second and central sets of tabs.

* * * * *